United States Patent [19]

Imanari et al.

[11] Patent Number: 4,460,706
[45] Date of Patent: Jul. 17, 1984

[54] CATALYST FOR THE PRODUCTION OF STYRENE

[75] Inventors: Makoto Imanari; Makoto Takiguchi, both of Ami, Japan

[73] Assignee: Mitsubishi Petrochemical Co., Ltd., Tokyo, Japan

[21] Appl. No.: 484,310

[22] Filed: Apr. 12, 1983

[30] Foreign Application Priority Data

Apr. 13, 1982 [JP] Japan .................................. 57-61393

[51] Int. Cl.³ .............................................. B01J 23/10
[52] U.S. Cl. .................................. 502/304; 502/330; 502/336; 502/344; 585/444
[58] Field of Search ............... 252/472, 473, 474, 462; 502/384, 330, 338, 344

[56] References Cited

U.S. PATENT DOCUMENTS

| | | | |
|---|---|---|---|
| 3,798,178 | 3/1974 | Soderquist et al. | 252/472 |
| 3,904,552 | 9/1975 | O'Hara | 252/462 |
| 4,144,197 | 3/1979 | Riesser | 252/462 |

Primary Examiner—Delbert E. Gantz
Assistant Examiner—Anthony McFarlane
Attorney, Agent, or Firm—Oblon, Fisher, Spivak, McClelland & Maier

[57] ABSTRACT

A catalyst for the production of styrene comprising 40–87.5 % by weight of iron oxide as $Fe_2O_3$, 11–50% by weight of cerium oxide as $Ce_2O_3$, and 1.5–40% by weight of potassium oxide as $K_2O$. By use of the catalyst, styrene can be produced at high conversions and high selectivies under reaction conditions wherein the amount of steam used as a source of heat is reduced.

9 Claims, No Drawings

CATALYST FOR THE PRODUCTION OF STYRENE

BACKGROUND OF THE INVENTION

1. Field of the Invention

This invention relates to a catalyst for the production of styrene.

2. Description of the Prior Art

Styrene is produced by catalytically dehydrogenating ethylbenzene with heat from steam. The catalysts used for the reaction are widely known as described in, for example, "Yuki Gosei Kagaku (Organic Synthetic Chemistry)", Vol. 36, page 768(1978) and Japanese patent publication (OPI) Nos. 120,887/'74 and 129,190/'78. Also processes for the production of styrene are widely known as described in, for example, "Aromatics", Vol. 32, page 150(1980); Kirk-Othmer, "Encyclopedia of Chemical Technology", Vol. 19, page 54(1969); Japanese patent publication (OPI) No. 135,427/'81, etc.

The known catalysts can give a high conversion and a high selectivity to styrene only when the reaction is performed in the presence of a large amount of steam, that is, when the dehydrogenation reaction is performed at a steam/ethylbenzene molar ratio of higher than 10, preferably of 10 to 20. In this case, however, a large amount of steam is used and hence a very large amount of heat is lost without being recovered. Accordingly, from the economic viewpoint, a catalyst capable of effectively performing the dehydrogenation of ethylbenzene under conditions wherein the steam/ethylbenzene mole ratio is as low as possible has been desired, but a catalyst capable of providing a high conversion and a high selectivity to styrene under these conditions and which has excellent durability has not yet been developed. Also, the above-mentioned Japanese patent publication (OPI) No. 135,427/'81 discloses that styrene can be produced with a reduced amount of steam but the catalyst used in the process has the disadvantages described above and the process disclosed therein is not satisfactory. A need therefore continues to exist for a more effective means of dehydrogenating ethylbenzene to styrene.

SUMMARY OF THE INVENTION

One object of the present invention is to provide a mixed oxide catalyst of excellent durabilty which enables the production of styrene by the dehydrogenation of ethylbenzene in the presence of reduced amounts of steam.

Briefly, the object and other objects of the invention as hereinafter will become more readily apparent can be attained by a catalyst which is useful for the production of styrene by the catalytic dehydrogenation of ethylbenzene by heating the same in the presence of steam, which comprises 40 to 87.5% by weight of iron oxide as $Fe_2O_3$, 11 to 50% by weight of cerium oxide as $Ce_2O_3$, and 1.5 to 40% by weight of potassium oxide as $K_2O$.

In another embodiment of this invention, a process is provided for producing styrene by the catalytic dehydrogenation of ethylbenzene with steam, which comprises performing the dehydrogenation reaction at a steam/ethylbenzene molar ratio of 3 to 9 in the presence of a catalyst comprising 40 to 87.5% by weight of iron oxide as $Fe_2O_3$, 11 to 50% by weight of cerium oxide as $Ce_2O_3$, and 1.5 to 40% by weight of potassium oxide as $K_2O$.

DETAILED DESCRIPTION OF THE INVENTION

The catalyst of this invention contains iron. cerium, and potassium as the components in the above described amounts. The raw materials for preparing the catalyst are as follows.

Suitable iron sources include iron oxide and iron compounds which can be converted into iron oxide by heating, such as ferric oxide, triiron tetraoxide, ferrous oxide, the hydrides thereof, ferrous hydroxide, ferric hydroxide, and the like. Also, nitrate, sulfate, halide, organic acid salts, alcoholates, etc., of iron can be used as the iron source after converting these materials into the oxides by heating the compounds to decompose the same to the oxides or by converting the compounds into hydroxides by hydrolysis with aqueous ammonia or the like. Furthermore, metallic iron can be used by dissolving it in nitric acid, or the like, and then hydrolyzing the resulting salt with aqueous ammonia or the like to the hydroxide.

Suitable cerium sources, includes oxides of cerium and other cerium compounds which can at least be partially converted into the oxide during the preparation of the catalyst such as the hydroxide, carbonate, hydrogencarbonate, oxalate, or nitrate compound. Another cerium source is the crude cerium oxide obtained from the refining of rare earth metals. The crude cerium oxide usually contains other light rare earth metals (La to Tb) and also 45–85% by weight of cerium oxide. The crude cerium oxide is normally marketed as abrasives or the like.

Suitable potassium sources include the carbonate, hydrogencarbonate, and nitrate compounds of potassium, as well as the composite oxides or composite carbonates of potassium and iron, calcium or bismuth.

In order to prepare a catalyst within the scope of the invention the desired oxides are selected so that the amount of $Fe_2O_3$ ranges from 40–87.5% by weight, the amount of $Ce_2O_3$ ranges from 11–50% by weight and the amount of $K_2O$ ranges from 1.5–40% by weight. When $Fe_2O_3$, $Ce_2O_3$, and $K_2O$ are in the ranges of 45–80% by weight, 11–45% by weight, and 6–35% by weight, respectively, more preferred results are obtained. When more than 11% by weight of cerium oxide as $Ce_2O_3$ is used together with iron and potassium as the components for the catalyst of this invention, the catalyst product exhibits excellent durability and also achieves a high conversion and a high selectivity of ethylbenzene to styrene at low molar ratios of steam to ethylbenzene.

The catalyst of this invention may further contain bismuth and/or calcium in an amount not over 25% by weight, preferably an amount of 1–20% by weight as $Bi_2O_3$ and/or CaO in addition to the foregoing primary components. Suitable bismuth sources include bismuth oxide and a material which can at least partially form bismuth oxide by decomposition during the preparation of the catalyst such as, for example, bismuth nitrate, bismuth sulfate, bismuth carbonate, or the like. Also, suitable calcium sources include calcium nitrate, calcium carbonate, calcium oxide, compounds of calcium and iron, and the like.

When bismuth and/or calcium is added to the catalyst of this invention in an amount not over 25% by weight as Bi₂O₃ and/or CaO, the selectivity for styrene is further improved.

The composition of the catalyst of this invention can be determined by measuring iron, cerium, potassium, bismuth, calcium or the like in the catalyst by any ordinary elemental analytical method such as X-ray fluorescence, atomic absorption, or the like, and converting these values into the quantities for the corresponding oxides in the catalyst.

The catalyst of this invention can be prepared by any conventional technique employed generally for preparing this kind of catalyst.

For example, after adding a desired amount of cerium hydroxide and a desired amount of potassium carbonate dissolved in a proper amount of water to a desired amount of ferric hydroxide, the mixture is stirred, kneaded and evaporated to dryness. The dried mixture is pulverized, stirred with the addition of a proper amount of water, kneaded to provide a moldable paste, and then extrusion-molded. The molded product is dried for 2–48 hours at about 120° C. and then calcined for about 3 hours at a definite calcining temperature, e.g., about 1,000° C. After cooling, the product is cut into proper lengths before use in the reaction.

The catalyst of this invention can be used in any form normally used as an ordinary fixed bed catalyst, and alternative forms such as a globular form, tablet form, a macaroni form, a honeycomb form, a star form, a single mass, or the like.

The catalyst of this invention may be supported on a carrier. In general, as the thickness of the catalyst becomes thinner, the effective utilization of the catalyst and the selectivity for styrene are improved. Hence, it is preferred that the catalyst be supported on a carrier at a thickness of about 0.1 to 2 mm. The form of the carrier used may be any one of a variety of shapes used in the prepration of supported catalysts such as, for example, a honeycomb form, a macaroni form, a globular form, a star form, or the like. That is, any carrier having a sufficient strength for carriers for catalysts may be used. Suitable examples of carrier materials include α-alumina, γ-alumina, silica-alumina, titania, magnesia, cordierite, silica, diatomaceous earth, clay, cerite, and the like, but the carrier used in this invention is not limited to these materials. The carrier may be mixed with the catalyst material and molded for use.

In the preparation of the catalyst of this invention, the calcining temperature is particularly important. It is preferred that the calcining temperture during the preparation of the catalyst range from 800° C. to 1,200° C., particularly 900° C. to 1,100° C. If the calcining temperature is lower than 800° C., the reduction in activity is serious, while if the calcining temperature is higher than 1,200° C., the initial activity is reduced.

The catalyst of this invention can be used under ordinary reaction conditions for the dehydrogenation of ethylbenzene. That is, the reaction conditions in which the steam/ethylbenzene mole ratio ranges from 3 to 20, the reaction temperature is 500° to 700° C., and the reaction pressure is 0.1 to 5 atms may be employed, but the greatest catyalytic activity is attained when the catalyst is used at a steam/ethylbenzene mole ratio of 3 to 9, preferably 5 to 7.5. Also, it is preferred that the feed rate of ethylbenzene be in the range of 0.1 to 5 hr$^{-1}$ expressed as the liquid hourly space velocity (LHSV).

Obviously, numerous modifications and variations of the present invention are possible in light of the above teachings. It is therefore to be understood that within the scope of the appended claims, the invention may be practiced otherwise than as specifically described herein.

The reactions in the following examples were performed by the following manner under normal pressure. A 30 ml amount of a granular catalyst (having grain sizes of about 0.84 to 1.68 mm) was packed into a stainless steel (SUS 316) flow-type reaction pipe having an inside diameter of 27 mm and a length of 480 mm, and while heating the reaction pipe in an electric furnace, water and ethylbenzene were introduced into the reaction tube at the desired catalyst bed temperature at an LHSV of ethylbenzene of 1 hrhu −1 to perform the reaction. The gaseous reaction mixture from the bottom of the reaction tube was cooled to provide a liquid product and a gaseous product. The liquid product and the gaseous product thus obtained were separatley analyzed by a gas chromatographic technique. Moreover, the following results were calculated by the following equations from data obtained in each experiment.

$$EB \text{ Conversion (mole \%)} = \frac{A^* - B^*}{A^*} \times 100$$

$$SM \text{ Yield (mole \%)} = \frac{C^*}{A^*} \times 100$$

$$SM \text{ Selectivity (mole \%)} =$$

$$\frac{C^*}{A^* - B^*} \times 100 = \frac{SM \text{ yield}}{EB \text{ conversion}} \times 100$$

wherein
EB=ethylbenzene
SM=stryene
A*=supplied ethylbenzene (mole)
B*=discharged ethylbenzene (mole)
C*=produced styrene (mole)

EXAMPLE 1

To 3,165 ml of an ice-cooled aqueous solution of 51% by weight nitric acid was added 360 g of iron powder with stirring and the resultant mixture was neutralized by the addition of 3 normal aqueous ammonia. The precipitate which formed was collected by filtration and sufficiently washed with distilled water to provide an iron hydroxide cake. A solution of 500 g of cerium nitrate (Ce(NO₃)₃.6H₂O) dissolved in 1,200 ml of ice-cooled water was neutralized by the addition of 3 normal aqueous ammonia and the precipitate thus formed was sufficiently washed with distilled water to provide a cerium hydroxide cake. To 336.3 g of the iron hydroxide cake (80 g as Fe₂O₃) thus obtained was added 46.6 g of the cerium hydroxide cake (18.2 g as Ce₂O₃) and after further adding thereto a solution of 15.4 g of potassium carbonate (10.5 g of K₂O) dissolved in 70 ml of distilled water, the resultant mixture was heated while kneading to sufficiently evaporate water. After drying the mixed cake thus obtained, the mixed cake was wetted by the addition of a proper amount of distilled water, wet-ground for 2 hours by means of a grinder, and then extrusion-molded into an elongated mass of 3 mm in diameter. The molded product thus obtained was dried and then calcined for 3 hours at 900° C. in a muffle furnace. The catalyst thus obtained had a composition consisting of iron, cerium, and potassium as Fe₂O₃, Ce₂O₃, and K₂O in amounts of Fe₂O₃=73.6% by weight, Ce₂O₃=16.7% by weight, and K₂O=9.7% by weight. The catalyst was ground into grain sizes of 0.84 to 1.68 mm and used for the reaction. The reaction conditions and the results obtained are shown in Table 1.

EXAMPLES 2-4

By following the same procedure as in Example 1, except that the calcining temperatures for preparing the catalysts were changed as shown in Table 1, catalysts were prepared and the dehydrogenation reaction was performed using each of the catalysts. The results obtained are shown in Table 1.

EXAMPLE 7

This example is based on a catalyst which contains bismuth as a component.

To 20 ml of an aqueous solution of about 20% by weight nitric acid were added 338.27 g of an iron hydroxide cake (80 g as $Fe_2O_3$) and 24.81 g of a cerium hydroxide cake (18.22 g as $Ce_2O_3$) each prepared in the same manner as described in Example 1 together with 15.41 g of potassium carbonate (10.5 g of $K_2O$) and 4.58 g of bismuth nitrate [$Bi(NO_3)_3.5H_2O$] (2.22 g as $Bi_2O_3$). The resultant mixture was sufficiently kneaded while

TABLE 1

| Example | Calcining temp. (°C.) | Reaction temp. (°C.) | H₂O/EB (molar ratio) | Reaction time (hr.) | EB conversion (mole %) | SM selectivity (mole %) | SM yield (mole %) |
|---|---|---|---|---|---|---|---|
| 1 | 900 | 650 | 12 | 50 | 88.9 | 83.1 | 73.9 |
| " | " | " | 6 | 50 | 80.2 | 83.7 | 67.1 |
| " | " | " | 6 | 500 | 80.5 | 83.7 | 67.4 |
| " | " | " | 5 | 50 | 74.3 | 84.2 | 62.6 |
| " | " | " | 5 | 500 | 74.2 | 84.5 | 62.7 |
| " | " | 600 | 12 | 50 | 76.9 | 91.4 | 70.3 |
| " | " | " | 6 | 50 | 58.6 | 93.7 | 54.9 |
| " | " | " | 6 | 500 | 58.9 | 93.2 | 54.9 |
| " | " | " | 5 | 50 | 52.0 | 94.4 | 49.1 |
| " | " | " | 5 | 500 | 51.8 | 95.1 | 49.3 |
| 2 | 1,000 | 650 | 12 | 50 | 84.8 | 86.5 | 73.3 |
| " | " | " | 5 | 50 | 73.7 | 85.0 | 62.6 |
| " | " | " | 5 | 500 | 73.5 | 85.2 | 62.6 |
| 3 | 750 | 650 | 12 | 50 | 91.8 | 57.3 | 52.5 |
| " | " | " | 5 | 50 | 70.9 | 81.7 | 57.9 |
| " | " | " | 5 | 500 | 66.2 | 82.4 | 54.5 |
| 4 | 1,350 | 650 | 12 | 50 | 84.8 | 86.5 | 73.3 |
| " | " | " | 5 | 50 | 65.1 | 87.1 | 56.7 |
| " | " | " | 5 | 500 | 64.7 | 87.3 | 56.5 |

EB = ethylbenzene, SM = styrene

EXAMPLES 5-6 AND COMPARATIVE EXAMPLES 1-2

By following the same procedure as described in Example 1 except that the composition of catalyst was changed as shown in Table 2, catalysts were prepared and the dehydrogenation reaction was performed using each of the catalysts thus prepared as in Example 1. The results obtained are shown in Table 2.

heating to evaporate water. After drying the cake thus obtained, the cake was wetted by the addition of a proper amount of distilled water, wet-ground for 2 hours by means of a grinder, and then extrusion-molded into an elongated mass 3 mm in diameter. The product thus obtained was dried and then calcined for 3 hours in a muffle furnace. The catalyst had the following composition: $Fe_2O_3=72.1\%$ by weight, $Ce_2O_3=16.4\%$ by weight, $Bi_2O_3=2.0\%$ by weight, and $K_2O=9.5\%$ by weight. The catalyst was pulverized into grain sizes of 0.84-1.68 mm for reaction use. The reaction conditions and the results obtained are shown in Table 3.

TABLE 2

| | Composition (wt. %) | | | Reaction temp. (°C.) | H₂O/HB (molar ratio) | Reaction time (hr.) | EB conversion (mole %) | SM selectivity (mole %) | SM yield (mole %) |
|---|---|---|---|---|---|---|---|---|---|
| | Fe₂O₃ | Ce₂O₃ | K₂O | | | | | | |
| Example 5 | 57.8 | 13.2 | 29.0 | 650 | 12 | 50 | 78.9 | 90.9 | 71.7 |
| " | " | " | " | " | 5 | 50 | 70.0 | 87.5 | 61.3 |
| " | " | " | " | " | 5 | 500 | 69.1 | 88.3 | 61.0 |
| Comparative example 1 | 88 | 2.4 | 9.7 | 650 | 12 | 20 | 88.5 | 72.0 | 63.7 |
| Comparative example 1 | " | " | " | " | 5 | 20 | 60.9 | 87.5 | 53.3 |
| Comparative example 1 | " | " | " | " | 5 | 100 | 49.4 | 84.4 | 41.7 |
| Comparative example 2 | 81.5 | 8.8 | 9.7 | 650 | 12 | 20 | 88.7 | 75.2 | 66.7 |
| Comparative example 2 | " | " | " | " | 5 | 20 | 67.5 | 80.9 | 54.6 |
| Comparative example 2 | " | " | " | " | 5 | 100 | 55.5 | 80.9 | 44.8 |
| Example 6 | 48 | 42.3 | 9.7 | 650 | 12 | 20 | 87.8 | 66.0 | 57.9 |
| " | " | " | " | " | 5 | 20 | 73.7 | 81.7 | 60.2 |
| " | " | " | " | " | 5 | 100 | 73.5 | 81.7 | 60.0 |

EB = ethylbenzene, SM = styrene

EXAMPLE 8

By the same manner as described in Example 7, a catalyst having the composition of $Fe_2O_3=63.0\%$ by weight, $Ce_2O_3=14.4\%$ by weight, $Bi_2O_3=14.4\%$ by weight, and $K_2O=8.3\%$ by weight was prepared and a dehydrogenation reaction was performed using the catalyst. The results are shown in Table 3.

EXAMPLE 9

By the same procedure as described in Example 7, except that 3.96 g of calcium carbonate (2.22 g of CaO) was used in place of a nitric acid solution of bismuth nitrate, a catalyst having the composition of $Fe_2O_3=72.1\%$ by weight, $Ce_2O_3=16.4\%$ by weight, $CaO=2\%$ by weight, and $K_2O=9.5\%$ by weight was prepared and a dehydrogenation reaction was performed by the same procedure describe in Example 7. The results obtained are shown in Table 3.

EXAMPLE 10

By the same procedure as described in Example 9, a catalyst having the composition of $Fe_2O_3=63.0\%$ by weight, $Ce_2O_3=14.4\%$ by weight, $CaO=14.4\%$ by weight, and $K_2O=8.3\%$ by weight was prepared and a dehydrogenation reaction was performed as described in Example 7. The results obtained are shown in Table 3.

bonate $[Ce_2(CO_3)_3.8H_2O]$, 9.65 g of cobaltous carbonate $(CoCO_3)$, 15.2 g of vanadium pentoxide, 93.68 g of potassium carbonate $(K_2CO_3)$, and 12.16 g of chromium oxide $(Cr_2O_3)$. The resultant mixture was wet-ground by means of a grinder, extrusion-molded, and the product thus obtained was calcined for 4 hours at 510° C. and then for 4 hours at 790° C. in a muffle furnace. The catalyst obtained had a composition of $Fe_2O_3=59.2\%$ by weight, $K_2O=12.6\%$ by weight, $V_2O_5=3.0\%$ by weight, $MoO_3=2.4\%$ by weight, $Ce_2O_3=19.2\%$ by weight, $CoO=1.2\%$ by weight, and $Cr_2O_3=2.4\%$ by weight. A dehydrogenation reaction was performed using the catalyst as described in Example 1. The results obtained are shown in Table 4.

COMPARATIVE EXAMPLE 4

A catalyst was prepared by the same manner described in Example 4, except that the final calcining temperature for the catalyst in Comparative Example 3 was changed to 900° C., which is the preferred calcining temperature of this invention and the dehydrogenation reaction was performed as described in Example 4 using the catalyst. The results obtained are shown in Table 4.

TABLE 1

| Comparative Example | Calcining temp. (°C.) | Reaction temp. (°C.) | H₂O/EB (molar ratio) | Reaction time (hr.) | EB conversion (mole %) | SM selectivity (mole %) | SM yield (mole %) |
|---|---|---|---|---|---|---|---|
| 3 | 790 | 650 | 12 | 50 | 80.7 | 93.7 | 75.6 |
| " | " | " | 5 | 50 | 37.8 | 84.6 | 32.0 |
| " | " | " | 5 | 150 | 35.4 | 84.6 | 29.9 |
| " | " | 600 | 12 | 50 | 51.5 | 97.4 | 50.2 |
| " | " | " | 5 | 50 | 22.2 | 94.6 | 21.0 |
| " | " | " | 5 | 150 | 20.4 | 93.9 | 19.2 |
| 4 | 900 | 650 | 12 | 50 | 72.8 | 95.5 | 69.5 |
| " | " | " | 5 | 50 | 44.0 | 84.8 | 37.3 |
| " | " | " | 5 | 150 | 39.7 | 82.8 | 32.9 |
| " | " | 600 | 12 | 50 | 41.5 | 97.4 | 40.4 |

EB = ethylbenzene, SM = styrene

From the results of the foregoing examples and comparative examples, it is clear that the catalysts of this invention exhibit excellent characteristics.

TABLE 3

| Example | Fe₂O₃ | Ce₂O₃ | Bi₂O₃ or CaO | K₂O | Reaction temp. (°C.) | H₂O/EB (molar ratio) | Reaction time (hr.) | EB conversion (mole %) | SM selectivity (mole %) | SM yield (mole %) |
|---|---|---|---|---|---|---|---|---|---|---|
| 7 | 72.1 | 16.4 | 2.0* | 9.5 | 650 | 12 | 50 | 89.7 | 81.8 | 73.3 |
| " | " | " | 2.0* | " | " | 5 | 50 | 72.3 | 86.5 | 62.5 |
| " | " | " | 2.0* | " | " | 5 | 500 | 72.1 | 86.6 | 62.4 |
| 8 | 63.0 | 14.4 | 14.4* | 8.3 | 650 | 12 | 50 | 87.8 | 88.9 | 78.1 |
| " | " | " | 14.4* | " | " | 5 | 50 | 71.5 | 87.1 | 62.3 |
| " | " | " | 14.4* | " | " | 5 | 500 | 71.7 | 87.0 | 62.4 |
| 9 | 72.1 | 16.4 | 2.0** | 9.5 | 650 | 12 | 50 | 91.5 | 83.4 | 76.3 |
| " | " | " | 2.0** | " | " | 5 | 50 | 64.0 | 90.6 | 58.0 |
| " | " | " | 2.0** | " | " | 5 | 500 | 63.8 | 91.0 | 58.1 |
| 10 | 63.0 | 14.4 | 14.4** | 8.3 | 650 | 12 | 50 | 88.1 | 87.6 | 77.2 |
| " | " | " | 14.4** | " | " | 5 | 50 | 64.1 | 91.0 | 58.6 |
| " | " | " | 14.4** | " | " | 5 | 500 | 65.0 | 91.0 | 59.2 |

EB = ethylbenzene, SM = styrene
*Bi₂O₃, **CaO

COMPARATIVE EXAMPLE 3

A catalyst was prepared as follows according to the method described in Example VI-9 of Japanese patent publication (OPI) No. 129,190/'78.

To 300 g of red iron oxide having a surface area of 5.3 m²/g and a mean grain size of 1 μm were added 12.16 g of molybdenum trioxide $(MoO_3)$, 358.23 g of ceric car-

EXAMPLE 11

A catalyst was prepared by the same manner described in Example 1, except that 18.9 g of a commercially available crude cerium oxide composition: (made by Mitsui Mining & Smelting Co., Ltd.) was used as a substitute for the cerium hydroxide cake of the example.

The crude cerium oxide had the composition of $CeO_2 = 78.1\%$ by weight, $Nd_2O_3 = 9.9\%$ by weight, $La_2O_3 = 8.4\%$ by weight, $Pr_6O_{11} = 3.2\%$ by weight, and $Sm_2O_3 = 0.4\%$ by weight, and a slight amount of $Fe_2O_3$ and other materials. The catalyst had the composition of iron, cerium, potassium, neodymium, lanthanum, praseodymium, and samarium as $Fe_2O_3 = 73.6\%$ by weight, $Ce_2O_3 = 13.0\%$ by weight, $K_2O = 9.7\%$ by weight, $Nd_2O_3 = 1.7\%$ by weight, $La_2O_3 = 1.5\%$ by weight, $Pr_6O_{11} = 0.6\%$ by weight, and $Sm_2O_3 = 0.1\%$ by weight. The catalyst was ground into grain sizes of 0.84–1.68 mm and used for the dehydrogenation reaction.

The reaction conditions and the results obtained were as follows:

Reaction temperature: 650° C.
$H_2O$/ethylbenzene (molar ratio): 6
Reaction time: 500 hours
Ethylbenzene conversion: 79.2 mole %
Styrene selectivity: 86.0%
Styrene yield: 68.1 mole %

From the foregoing results, it is clear that the catalyst prepared from crude cerium oxide as a substitute cerium source also exhibits excellent catalytic action.

What is claimed as new and desired to be secured by Letters Patent of the United States is:

1. A catalyst for the production of styrene by the catalytic dehydrogenation of ethylbenzene by heating with steam, consisting essentially of:
   40 to 87.5% by weight of iron oxide as $Fe_2O_3$, 11 to 50% by weight of cerium oxide as $Ce_2O_3$, and 1.5 to 40% by weight of potassium oxide as $K_2O$.

2. The catalyst of claim 1 wherein the catalyst is prepared by calcining the mixed oxide mass of the catalyst over a temperature range of 800° to 1200° C.

3. The catalyst of claim 1, wherein the catalyst is prepared by calcining the mixed oxide mass of the catalyst over a temperature range of 900° to 1100° C.

4. The catalyst of claim 1, which comprises 45–80% by weight $Fe_2O_3$, 11–45% by weight $Ce_2O_3$ and 6–35% by weight $K_2O$.

5. The catalyst of claim 1, wherein the mixed oxide catalyst is supported on a carrier.

6. The catalyst of claim 1, wherein the steam/ethylbenzene molar ratio during the dehydrogenation of ethylbenzene over said catalyst is within the range of 3 to 9.

7. The catalyst of claim 6, wherein the molar ratio range of steam to ethylbenzene is 5 to 7.5.

8. A catalyst for the production of styrene by the catalytic dehydrogenation of ethylbenzene by heating with steam, consisting essentially of:
   40 to 87.5% by weight of iron oxide as $Fe_2O_3$, 11 to 50% by weight of cerium oxide as $Ce_2O_3$, 1.5 to 40% by weight of potassium oxide as $K_2O$, and up to about 25% by weight of $Bi_2O_3$, CaO or mixture thereof.

9. The catalyst of claim 8, wherein the amount of CaO, $Bi_2O_3$ or mixtures thereof in said catalyst ranges from 1–20% by weight.

* * * * *